(12) United States Patent
Sanchez-Browning (10) Patent No.: US 6,280,422 B1
(45) Date of Patent: Aug. 28, 2001

(54) FEEDING APPARATUS WITH REPLACEABLE FEEDING BOTTLE

(76) Inventor: Maria Sanchez-Browning, 13621 Exotica La., Wellington, FL (US) 33414

( * ) Notice: Subject to any disclaimer, the term of this patent is extended or adjusted under 35 U.S.C. 154(b) by 0 days.

(21) Appl. No.: 08/906,423

(22) Filed: Aug. 5, 1997

Related U.S. Application Data (60) Provisional application No. 60/023,517, filed on Aug. 7, 1996.

(51) Int. Cl.[7] .................................................. A61M 5/00
(52) U.S. Cl. ...................... 604/257; 604/261; 604/403; 604/174; 215/11.4; 215/11.5; 137/845
(58) Field of Search ..................................... 604/257, 259, 604/260, 261, 262, 403, 404, 406, 407, 408, 409, 410, 174; 215/11.4, 11.5, 261, 271; 137/845

(56) References Cited

U.S. PATENT DOCUMENTS

| | | |
|---|---|---|
| 216,734 | 6/1879 | France . |
| 244,181 | 7/1881 | Carpenter . |
| 347,018 | 8/1886 | Ware . |
| 1,438,899 | 12/1922 | Cassidy . |
| 1,687,004 | 10/1928 | Briggs . |
| 2,493,380 | 1/1950 | Bailey . |
| 2,827,081 | 3/1958 | Little . |
| 3,200,860 | 8/1965 | Barton et al. . |
| 3,990,597 | 11/1976 | Barton . |
| 4,557,959 | 12/1985 | Kuehlein et al. . |
| 4,895,327 | * 1/1990 | Malone et al. ..................... 248/102 |
| 4,966,580 | 10/1990 | Turner et al. . |
| 5,135,125 | * 8/1992 | Andel et al. ........................ 215/100 |

* cited by examiner

*Primary Examiner*—Wynn Wood Coggins
*Assistant Examiner*—N. Kent Gring (57) ABSTRACT

A feeding apparatus for a patient having a surgically created stoma in the stomach. The apparatus enables feeding liquids of varying viscosities without a suction pump. The simplified, replaceable feeding bottle design makes the apparatus useable by hospital personnel and by patients at home. A decorative cover provides additional privacy.

13 Claims, 8 Drawing Sheets

FEEDING APPARATUS WITH REPLACEABLE FEEDING BOTTLE

CROSS-REFERENCE TO RELATED APPLICATION

This application claims the benefit of U.S. Provisional Pat. application Ser. No. 60/023,517, filed Aug. 7, 1996.

BACKGROUND OF THE INVENTION

1. Field of the Invention

The present invention relates to a feeding apparatus with a replaceable bottle for feeding a patient who has a surgically created stoma in the stomach or elsewhere in the digestive tract.

2. Description of the Prior Art

Patients who have undergone surgical procedures such as percutaneous, endoscopic or gastrostomy must be fed through a tube which is inserted into the patient's stomach or gastrointestinal (G.I.) tract. Feeding is accomplished by attaching a feeding apparatus to the inserted tube. Currently, two types of feeding apparatus are commonly used. One type generally comprises a collapsible plastic bag, similar to an I.V. bag. The bag is purchased filled with previously prepared, liquified food. The attached bag is placed above the patient and the liquified food is delivered by the force of gravity. A vacuum collapses the bag as the food exits therefrom. When the bag is empty, it is disconnected from the G.I. tube and disposed. However, the bag apparatus does not adequately deliver liquids of significant viscosity. Thus, the additional necessary viscous nutritional substances must be administered directly into the G.I. tube with a 60 c.c. syringe. This procedure is time-consuming as it must be repeated approximately 5 to 6 times per feeding. Also, this procedure must usually be performed by a nurse as it requires more effort than many patients are able to exert.

The second type of feeding apparatus delivers the liquified food from a bottle by means of a suction air pump. This apparatus is better than the bag in that it provides the patient with the ability to prepare a varying range of liquified foods. Thus, the patient can maintain a more balanced diet. However, the pump is noisy, expensive to rent, and not sufficiently portable.

Examples of previous patents for feeding devices include the following. U.S. Pat. No. 216,734, issued on Jun. 24, 1879, to Simon W. France, discloses a nursing-bottle into which air is admitted when a baby sucks milk out of the bottle through a nipple. U.S. Pat. No. 244,181, issued on Jul. 12, 1881, to Willard C. Carpenter, discloses a regulator for nursing-bottles which controls the amount of milk that a child sucks out of a bottle. U.S. Pat. No. 347,018, issued on Aug. 10, 1886, to Walter F. Ware, discloses a nursing bottle with a one-way valve that permits air to flow into the bottle as milk is sucked out. The instant invention is distinguishable from the foregoing inventions in that it is a device for supplying food directly into the G.I. tract, rather than through the patient's mouth. Also, the food is moved by gravity, rather than by suction.

U.S. Pat. No. 1,438,899, issued on Dec. 12, 1922, to Louis T. Cassidy, discloses a surgical appliance being an insulated vacuum bottle within which a liquid can be kept warm, with an outlet for the liquid, and an inlet for air to replace the liquid as it flows out. The instant invention is distinguishable in that it is designed to be permanently hung upside down. Also the present invention has an air inlet tube connected to the cap which extends upward to above the level of the fluid in the feeding bottle.

U.S. Pat. No. 1,687,004, issued on Oct. 9, 1928, to Marie Briggs, discloses a nursing bottle cover and nipple support which may be placed over a nursing bottle and tied on with a cord. The present invention is distinguishable in that it does not operate by suction. The cover of the instant invention is distinguishable in that it has peel-off strips by which it may be tied on the feeding bottle.

U.S. Pat. No. 2,493,380, issued on Jan. 3, 1950, to Theodore Bailey, discloses a thermally insulated nursing bottle which is reinforced with internal ribs. The instant invention is distinguishable in that it has external tubes through which food can flow out and air can flow in, with separate holes for the tubes, and it does not operate by suction.

U.S. Pat. No. 2,827,081, issued on Mar. 18, 1958, to Robert C. Little, discloses a parenteral fluid dispenser, having a hole for a tube for liquid to flow out of to the patient, and a hole for an air inlet. The instant invention is distinguishable in that it has a tube connected to the air inlet that extends upward to above the level of the fluid in the feeding bottle. Also, the Little patent is directed towards apparatus for injecting I.V. solutions, not towards apparatus for feeding.

U.S. Pat. No. 3,200,860, issued on Aug. 17, 1965, to Raymond W. Barton, Thomas A. Benjamin and Joe T. Herron, discloses a disposable nurser with a plurality of nipples and a filling apparatus for it. The instant invention is distinguishable as it is designed for long term use, does not include nipples and does not operate by suction.

U.S. Pat. No. 3,990,597, issued on Nov. 9, 1976, to Raymond W. Barton, discloses a container and gavage tube adapter with a vent for letting in air, for feeding a patient through the nose. The design of the Barton invention only permits the use of a liquid having a single, predetermined consistency. The instant invention is distinguishable in that it can be used in conjunction with a wide range of liquified foods of varying consistencies and viscosities.

U.S. Pat. No. 4,557,959, issued on Dec. 10, 1985, to Georg Kuehlin and Ernst Gerlach, discloses multilayer medical working means for containing or transporting a physiological material, which, unlike the instant invention, is not designed for feeding.

U.S. Pat. No. 4,966,580, issued on Oct. 30, 1990, to John J. Turner and Mary J.A. Turner, discloses an oral feeding appliance including a container and a tube from the container to a nipple to be placed in the patient's mouth. The instant invention is distinguishable in that it is designed to feed a patient through a surgically created opening in the gastrointestinal tract rather than through the mouth. Also, it does not require the use of pumps.

Therefore, a need exists for an easy-to-use and inexpensive apparatus for delivering nutritional liquids of various viscosities directly into a patient's G.I. tract. None of the above inventions and patents, taken either singly or in combination, is seen to describe the instant invention as claimed.

SUMMARY OF THE INVENTION

The present invention relates to a feeding apparatus by which a patient who is unable to ingest food orally, may be fed through a surgically created stoma in the stomach or elsewhere in the G.I. tract. The feeding apparatus primarily comprises a feeding bottle which has a main body and a neck with an opening; a feeding cap having two holes therethrough, and being sealingly attachable to the neck of the feeding bottle; a feeding tube in communication with the first hole of the feeding cap; an air inlet tube in communication with the second hole of the feeding cap to vent the feeding bottle and prevent the formation of a vacuum; and a flow control valve. After the feeding cap is attached to a filled feeding bottle, the feeding bottle is inverted above the patient to allow liquified food to flow through the feeding tube. The air inlet tube prevents a vacuum from forming in the feeding bottle. The flow control valve enables the patient or a nurse to control the amount of food flowing through the feeding tube. When the feeding bottle is empty, it is detached from the feeding cap and replaced with a full bottle. A storage cap is also provided to seal the feeding bottle during periods of non-use.

The feeding tube and the air inlet tube may be sealingly attached to the feeding cap with various connectors. However, it is preferable if the feeding cap and the two tubes are of a unitary construction for easier assembling of the feeding apparatus. It is also preferable if the cap and tubes are constructed of a transparent material, such as plastic. Transparency will enable visual confirmation of food flow and provide a more sterile appearance.

An adapter is attached to the opposite end of the feeding tube for connecting the feeding tube to the patient's G.I. tube. The adapter has a graded conical end for attachment to G.I. tubes of various internal diameter. Preferably, a transparent food flow indicator, such as an open ended cylinder, is disposed in communication with the feeding tube, to enable visual confirmation of the food flow through the feeding tube. It is also preferable if the adapter, food flow indicator and feeding tube are also of unitary construction.

A strap is provided which is sized and configured for supporting the feeding bottle with the neck oriented in a downward direction. Preferably, the strap should also possess a holding means, such as a loop or a clip. The holding means holds the air inlet tube to position the second end of the air inlet tube above the feeding bottle to prevent spillage of the liquid food therefrom. A handle is also attached to the strap. The handle enables the patient to either suspend the feeder from a stand for hand-free usage, or alternatively, carry the feeder for greater mobility.

A flow control valve is disposed in communication with one of either the air passage of the air inlet tube or the food-flow passage of the feeding tube. The flow control valve is selectively positionable between an open position for allowing communication through the passage, and a closed position for preventing communication though the passage. Placement of the flow control valve in communication with the air inlet tube stops food flow when closed by creating a vacuum in the feeding bottle. However, it is preferable if the flow control valve is disposed in communication with the feeding tube adjacent the adapter to enable convenient control by the patient.

The feeding bottle may be constructed of various materials such as glass or microwaveable plastic. The material may either be transparent or non-transparent. Preferably, the feeding bottle should include a volumetric scale on the side of the main body so that portions of food may be easily measured. The volumetric scale may depict English units, metric units, or both. For nontransparent embodiments of the feeding bottle, it is preferable if that portion of the main body where the volumetric scale is located is transparent. The volumetric scale may either be oriented for reading while the food is being filled into the feeding bottle, or it may be oriented for reading while the feeding bottle is inverted for use. Also, it is preferable if the feeding bottle includes a recessed or raised portion for easier gripping.

Additionally, the feeding bottle may be designed for multiple uses, or it may be disposable. A re-usable feeding bottle may be washed or sterilized after each use. Thereafter, the feeding bottle may be refilled with a wide variety of liquified foods, providing the patient with a more balanced diet. The filled bottle may be refrigerated as necessary and warmed in the microwave. Alternatively, pre-filled, disposable feeding bottles may be more convenient for patients with limited mobility who are unable to perform simple chores such as preparing the food or washing the feeding bottle. The use of disposable feeding bottles may also prove to be more efficient at hospitals and nursing homes, where preparing the food and washing the feeding bottles may prove too time-consuming for nurses or attendants.

Regardless of whether a re-usable or disposable bottle is employed, the present feeding apparatus provides an improved, straightforward feeding method. While the feeding cap and tubes still should be replaced every day for sanitary reasons, daily feedings only require that the old bottle be unscrewed from the feeding cap, and a new bottle be screwed onto the feeding cap. Thus four to six feeding bottles may be used in conjunction with each cap, eliminating the need to dispose of the cap and tubing after every use.

Finally, because the food must be converted to a liquified form for passage directly into the G.I. tract, the appearance of the food may be unpleasant. Thus, it is preferable if the feeding bottle is provided with a concealing means. The concealing means enables the patient and visitors to avoid looking at the contents of the feeding bottle, thereby reducing their embarrassment. This feature makes the portable feeding apparatus more acceptable for use in public locations.

The concealing means may comprise a decorative cover sized for fitted, removable attachment over the feeding bottle. Preferably, the decorative cover should additionally possess securing means, such as peelable adhesive strips, for securing the decorative cover over the feeding bottle. Alternatively, the feeding bottle may be constructed of a non-transparent material, such as white, opaque plastic. For non-transparent embodiments, the bottle itself serves as the concealing means, and no further cover is necessary. Also, in either embodiment, the concealing means, the bottle, or both may be further decorated to make the feeding apparatus more aesthetically pleasing, thereby aiding in cheering the patient.

Accordingly, it is a principal object of the invention to provide a means for feeding patients who are unable to take food orally.

Another objective of the invention is to provide a feeding apparatus which does not require a pump for delivering liquified foods of a wide range of viscosities.

It is another object of the invention to provide a feeding apparatus which can be operated either by the patient or by a nurse.

Still another object of the invention is to provide a means by which blenderized home-cooked meals may be provided to patients who have had ostomies.

It is a further object of the invention to provide a feeding apparatus which allows a patient to easily refrigerate and reheat the liquified food when desired.

It is still a further object of the invention to provide a portable feeding apparatus which may be used at a hospital, in the patient's home, or in public.

It is a further object of the invention to provide privacy to patients who must feed through a tube.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is a feeding apparatus with a removable feeding bottle for feeding a patient having a surgically created stoma in the stomach or elsewhere in the digestive tract.

Figure 1:
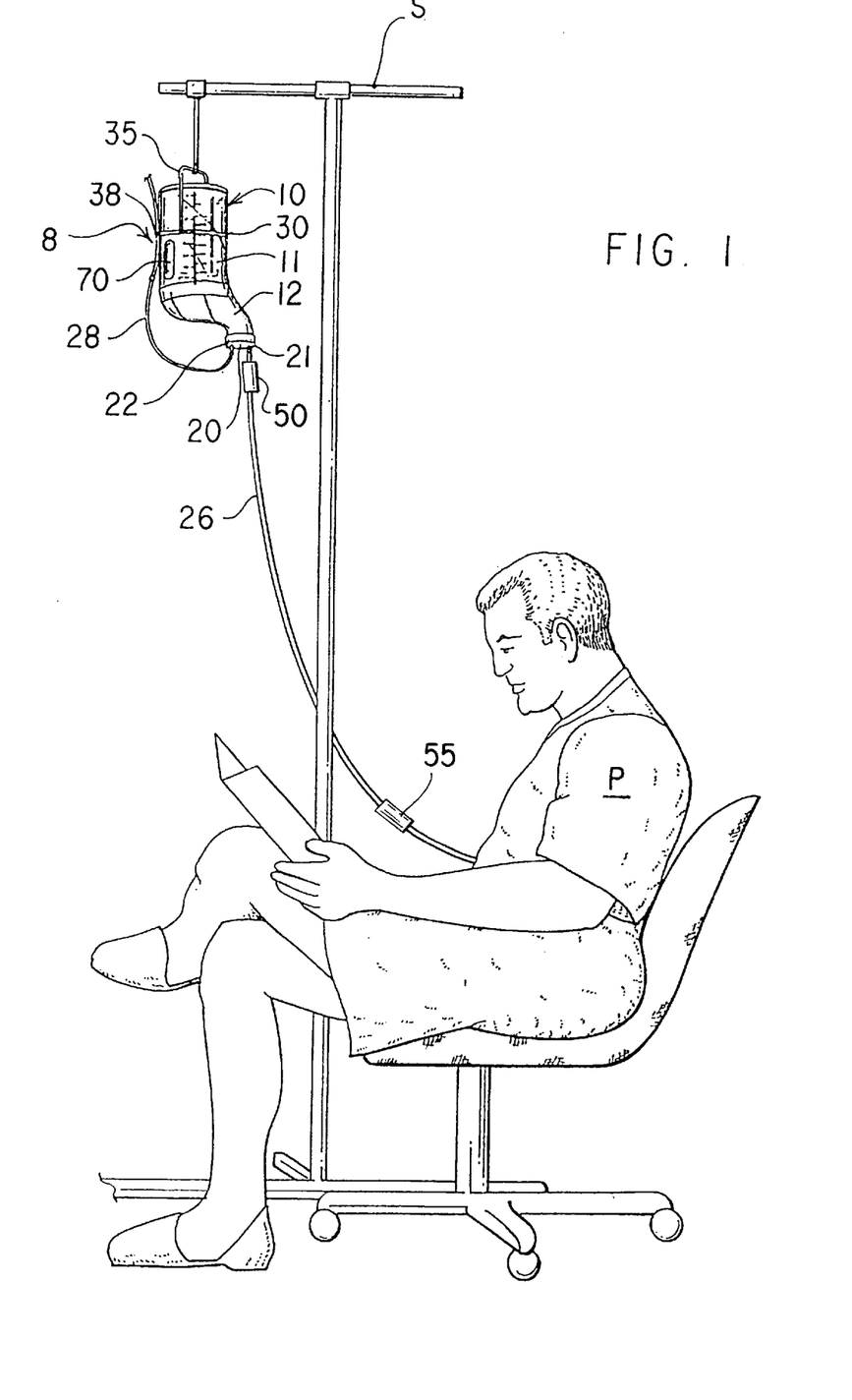
FIG. 1 is an environmental view of the feeding apparatus according to the present invention, depicting an embodiment wherein the feeding bottle has an off-center neck.

FIG. 1 is an environmental view of the feeding apparatus 8 according to the present invention. A feeding bottle 10 has a main body 11 and an off-center neck 12 with an opening. A feeding cap 20 is sealingly attached to the opening. The feeding cap has a first hole 21 and a second hole 22. A feeding tube 26 has a first end attached to the first hole 21 of the feeding cap 20, and has a second end (not shown) connected to a G.I. tube which is inserted into a patient's P surgically created stoma. An air inlet tube 28 has a first end attached to the second hole 22 of the feeding cap 20, and has a second end positioned above the feeding bottle 10 for venting. A strap 30 supports the feeding bottle 10, and a handle 35 is attached to the strap 30 for hanging the feeding bottle 10 from a stand S. The strap 30 is provided with a tube holder 38 for holding the second end of the air inlet tube 28 above the feeding bottle 10. A transparent food-flow indicator 50 is disposed in communication with the food-flow passage of the feeding tube 26 for enabling visual confirmation of the food flow through the feeding tube. A flow control valve 55 is disposed in communication with the food flow passage of the feeding tube 26. The flow control valve is disposed adjacent the second end of the feeding tube 26 to enable convenient control by the patient P. The main body 11 of the feeding bottle 10 has a recessed portion 70 for improved gripping.

Figures 2, 3, 4:
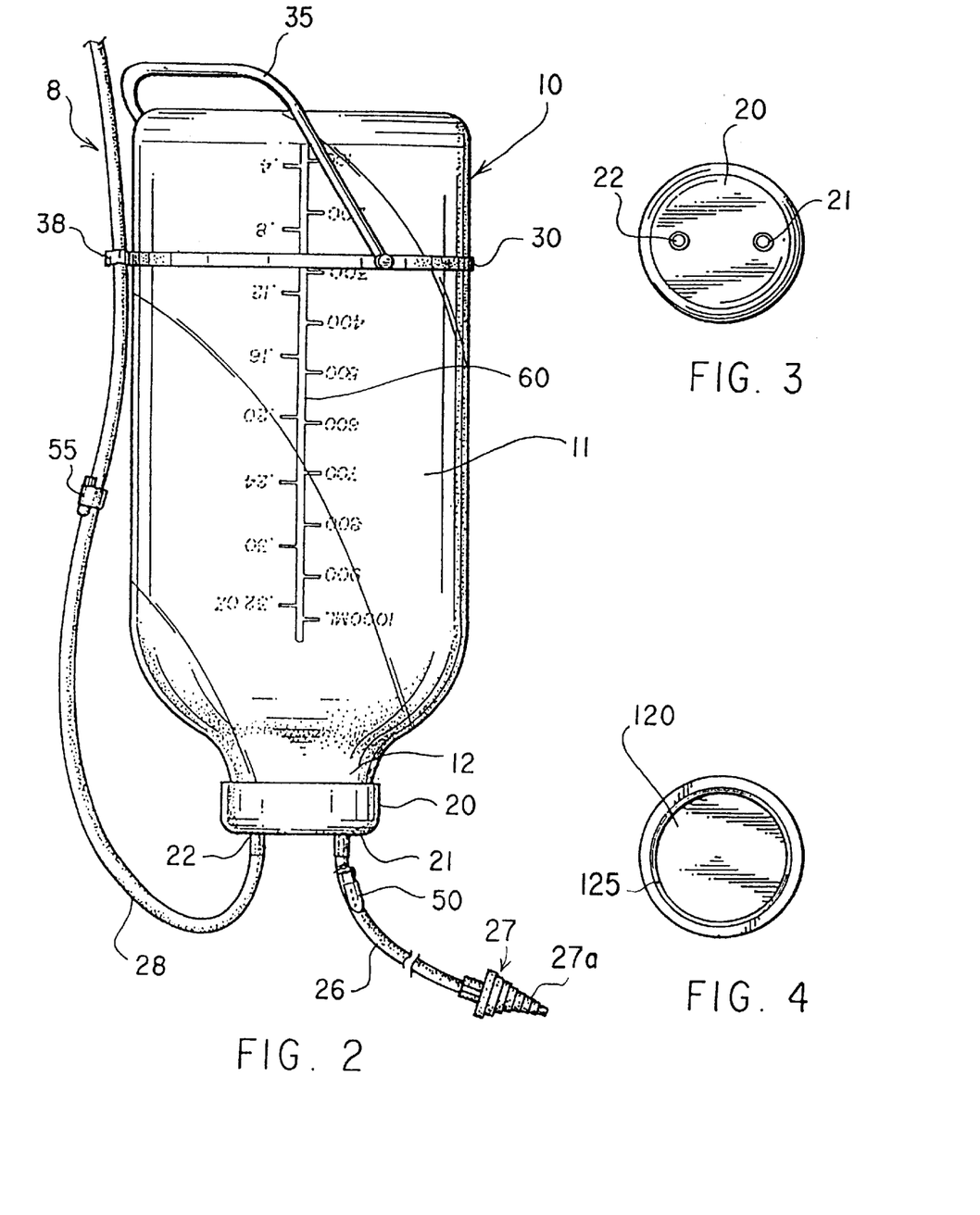
FIG. 2 is a front elevational view of the feeding apparatus, depicting an embodiment wherein the flow control valve is in communication with the air passage of the air inlet tube.
FIG. 3 is a bottom view of the feeding cap.
FIG. 4 is a top view of the storage cap.
Figure 5:
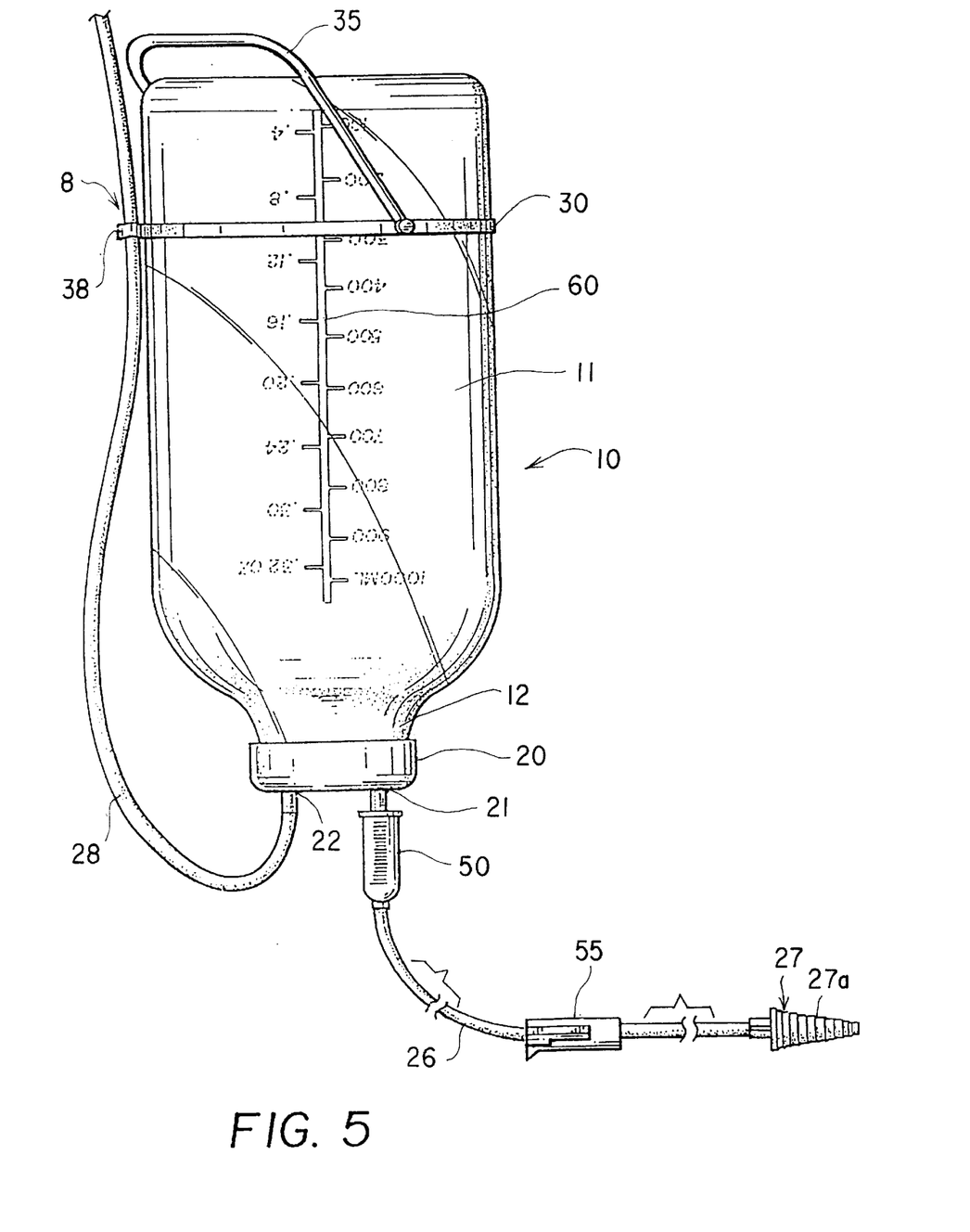
FIG. 5 is a front elevational view of the feeding apparatus, depicting an embodiment wherein the flow control valve is in communication with the food-flow passage of the feeding tube.
Figure 8:
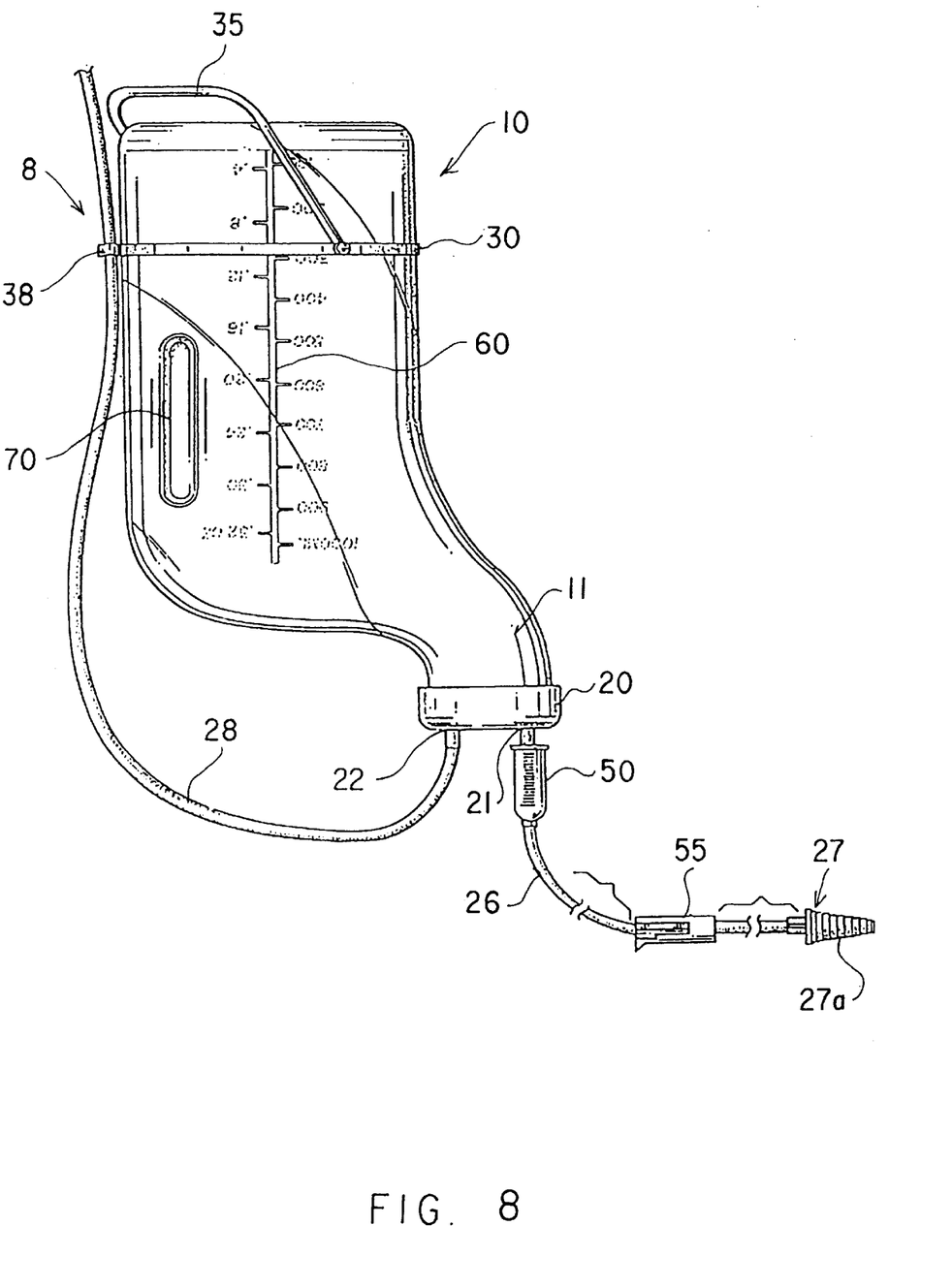
FIG. 8 is a front elevational view of the embodiment of the feeding bottle having an off-center neck.

FIG. 2, FIG. 5 and FIG. 8 are front elevational views of the feeding apparatus 8. FIG. 2 and FIG. 5 depict an embodiment of the feeding apparatus 8 wherein the feeding bottle 10 has an open neck 12 axially centered relative to the main body 11. FIG. 8 depicts an embodiment of the feeding apparatus 8 wherein the feeding bottle 10 has an open neck 12 which is off-center relative to the main body 11. In all three of FIG. 2, FIG. 5 and FIG. 8, the feeding cap 20 is sealingly attached to the opening of neck 12. The feeding cap has a first hole 21 and a second hole 22. The feeding tube 26 has a first end which is sealingly attached to the first hole 21 of the feeding cap 20, and in communication with a food flow passage (not shown). An 27 adapter is attached to the second end of the feeding tube 26. The adapter 27 has a graded conical end 27a, and an internal passage (not shown) running therebetween. The adapter 27 enables sealing connection of the feeding tube 26 with a G.I. tube inserted into a patient's stoma. The graded conical end 27a enables connection with G.I. tubes of varying internal diameter. A transparent food-flow indicator 50 is disposed in communication with the food-flow passage of the feeding tube 26 for enabling visual confirmation of the food flow through the feeding tube 26.

An air inlet tube 28 has a first end sealingly attached to the second hole 22 of the feeding cap 20, and has a second end positioned above the feeding bottle 10 for venting thereof. Referring to FIG. 2, a flow control valve 55 is disposed in communication with the air passage (not shown) of the air inlet tube 28. Closure of the flow control valve 55 blocks the air passage to create a vacuum in the feeding bottle 10, thereby stopping food flow. Referring to FIG. 5 and FIG. 8, the flow control valve 55 is disposed in communication with the food-flow passage (not shown) of the feeding tube 26. Closure of the flow control valve 55 blocks the food-flow passage to stop food flow.

In all three of FIG. 2, FIG. 5 and FIG. 8, a strap 30 supports the feeding bottle 10. The strap 30 is provided with a tube holding means 38 for holding the second end of the air inlet tube 28 above the feeding bottle 10. A handle 35 is attached to the strap 30 for hanging the feeding bottle 10. The feeding bottle 10 is generally opaque to conceal the contents thereof, but has a transparent volumetric scale 60 on the main body 11 for measuring food portions. FIG. 8 further depicts the inclusion of a recessed area 70 provided on the main body 11 of the feeding bottle 10 for improved gripping.

FIG. 3 and FIG. 4 depict two caps associated with the present invention. FIG. 3 is a bottom view of the feeding cap 20. The feeding cap 20 has a first hole 21 for attachment of the feeding tube 26 (not shown) and a second hole 22 for attachment of the air inlet tube 28 (not shown). FIG. 4 is a top view of the storage cap 120, which is used to seal the feeding bottle 10 when not in use. FIG. 4 depicts the internal threads 125 for screwing the storage cap 120 onto the feeding bottle 10.

Figure 6:
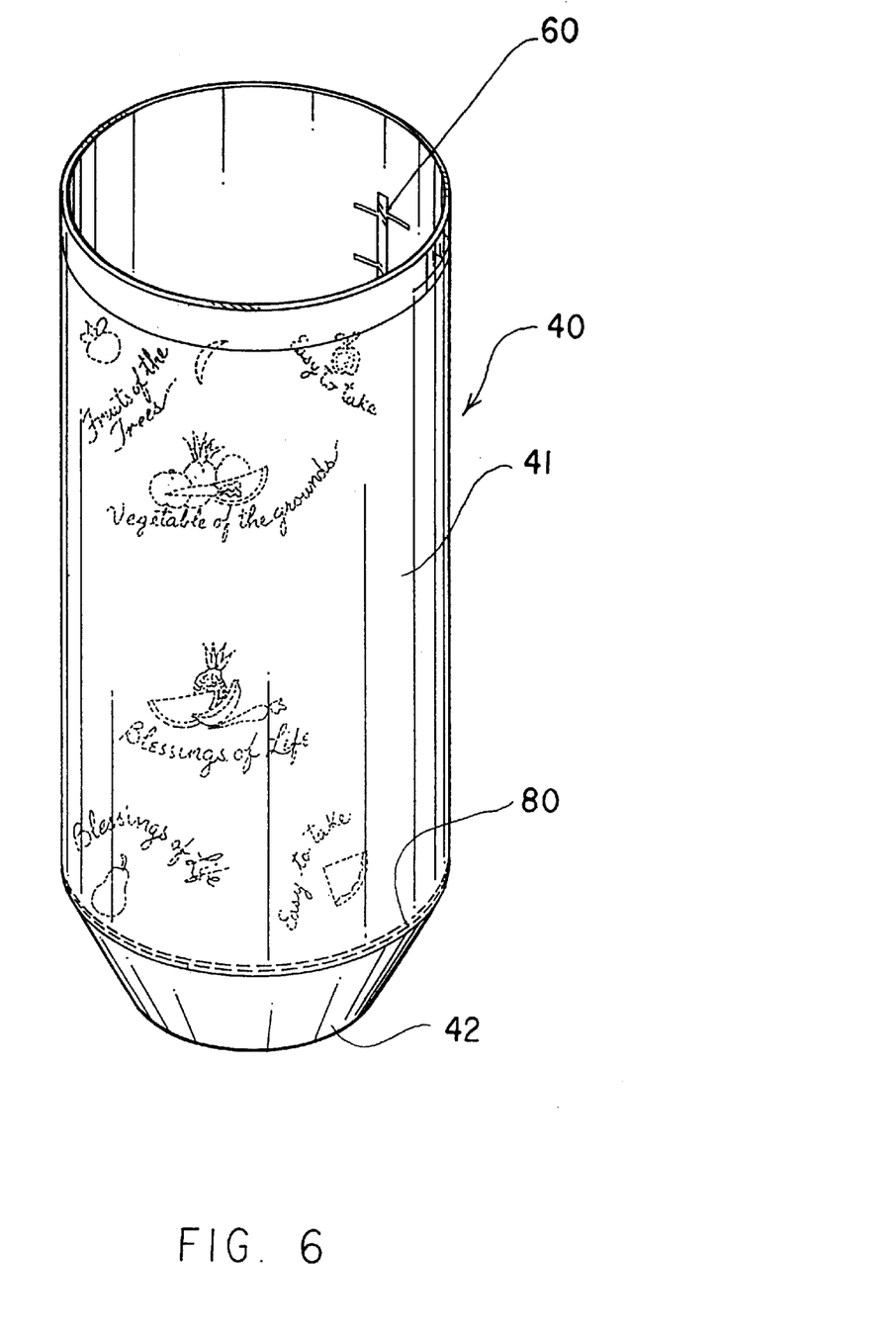
FIG. 6 is a front perspective view of the embodiment of the decorative cover for use with a feeding bottle having an axially centered neck.
Figure 7:
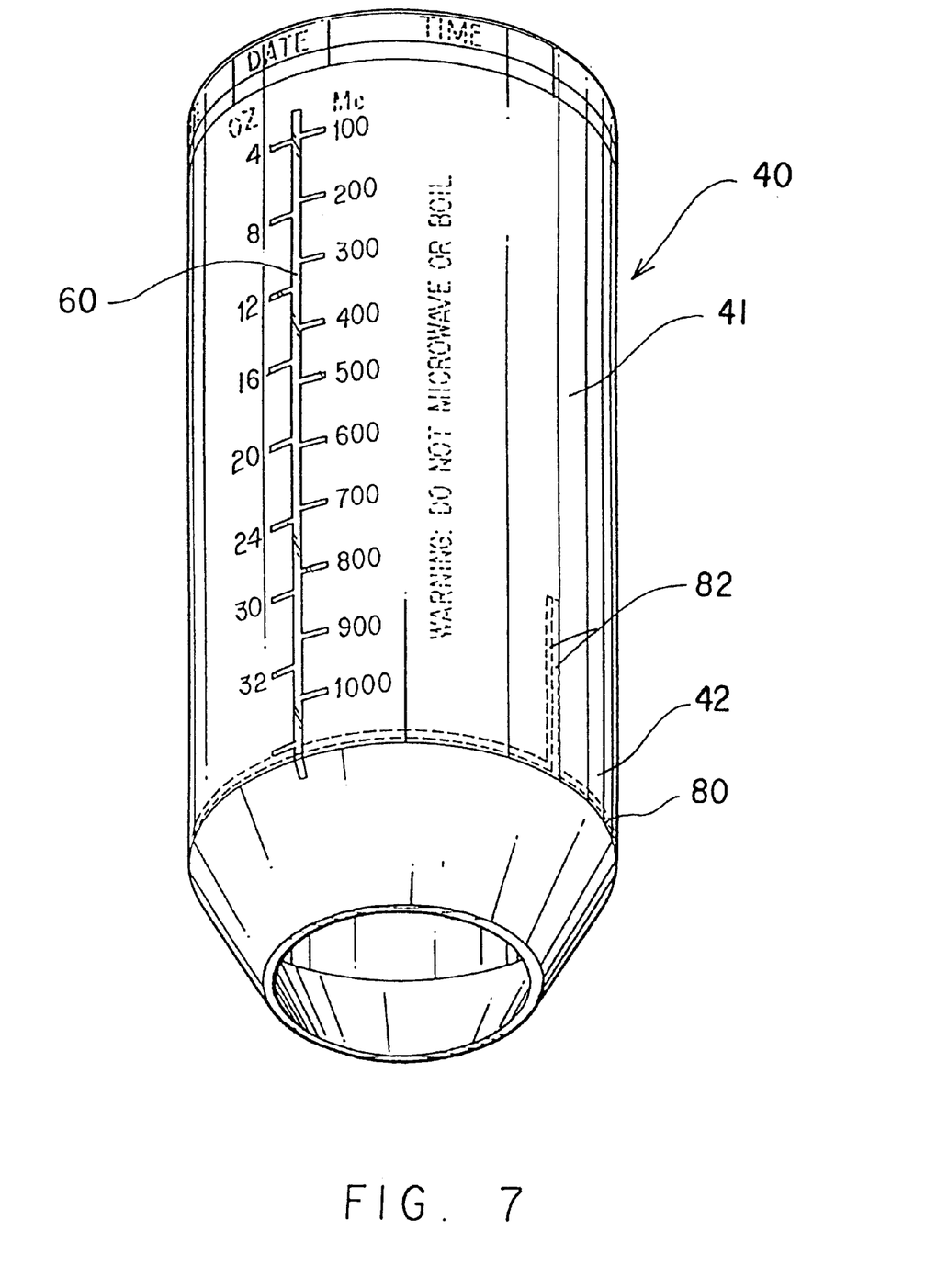
FIG. 7 is a rear perspective view of an embodiment of the decorative cover for use with a feeding bottle having an axially centered neck.

FIG. 6 and FIG. 7 are front and rear perspective views, respectively, of the embodiment of the decorative cover 40 for use with a feeding bottle 10 having an axially centered neck 12. The decorative cover 40 has a main-body-covering portion 41 and a neck-covering portion 42. Both the main-body-covering portion 41 and the neck-covering portion 42 are opaque. A volumetric scale 60 is disposed upon the main-body-covering portion 41. The volumetric scale 60 is transparent to permit visual confirmation of the volume of the food within the feeding bottle (not shown). A peelable adhesive strip 80 having a length greater than the circumference of the decorative cover 40 is attached circumferencially around the neck-covering portion 42 of the decorative cover 40. The peelable adhesive strip 80 has two opposing ends 82 peelably disposed upon the decorative cover 40. The opposing ends 82 may be peeled from the decorative cover 40 for adhesive re-attachment to the neck-covering portion 42 after the neck-covering portion 42 has been gathered together to reduce the circumference thereof for securing the decorative cover 40 over the feeding bottle (not shown). FIG. 6 further depicts decorative pictures and phrases printed upon the decorative cover 40. Referring to FIG. 7, the decorative cover has areas for including important information, such as the patient's name, date, and appropriate time for the feeding.

Figure 9:
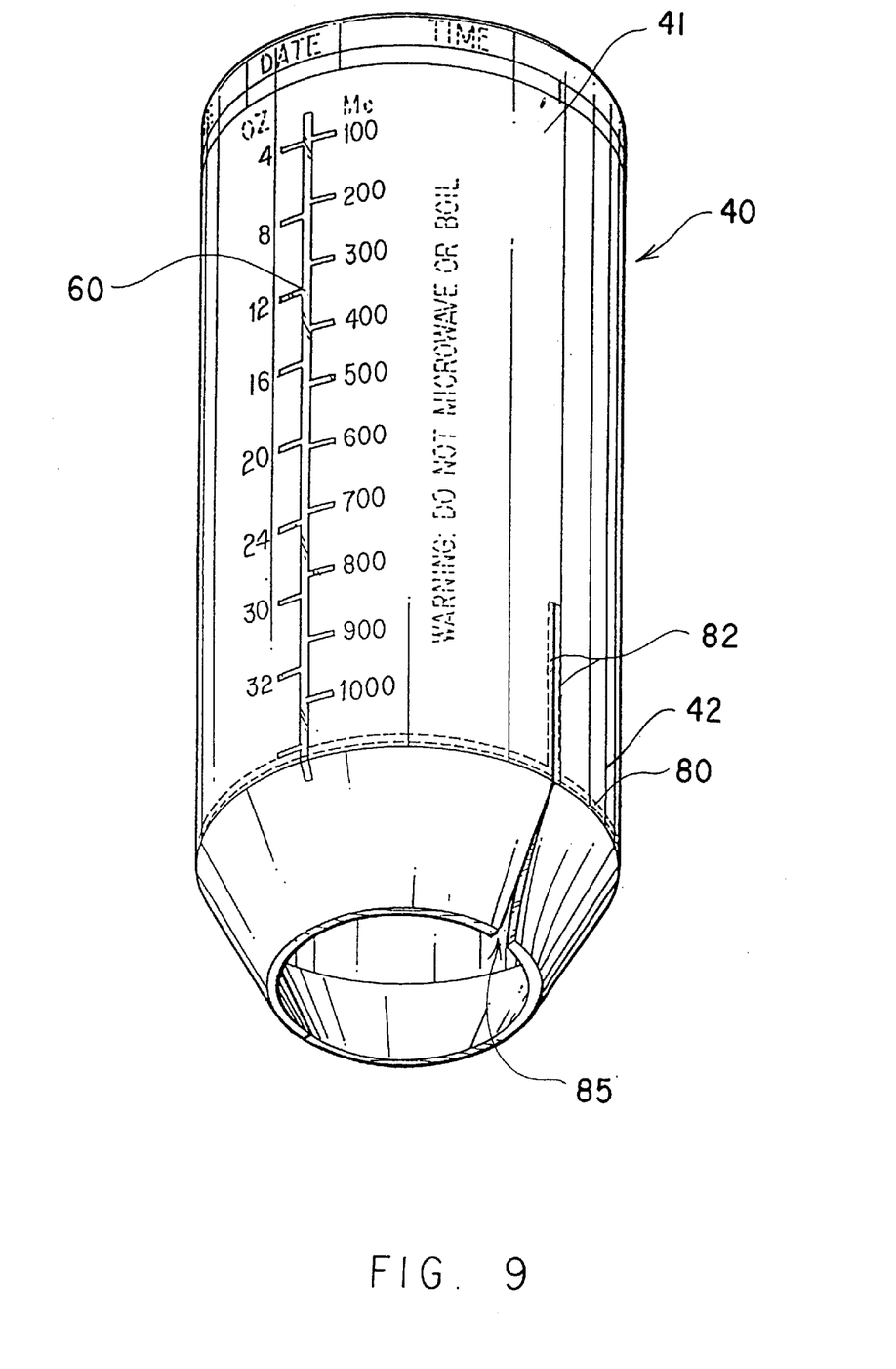
FIG. 9 is a rear perspective view of the embodiment of the decorative cover for use with the embodiment of the feeding apparatus wherein the feeding bottle has an off-center neck.
Figure 10:
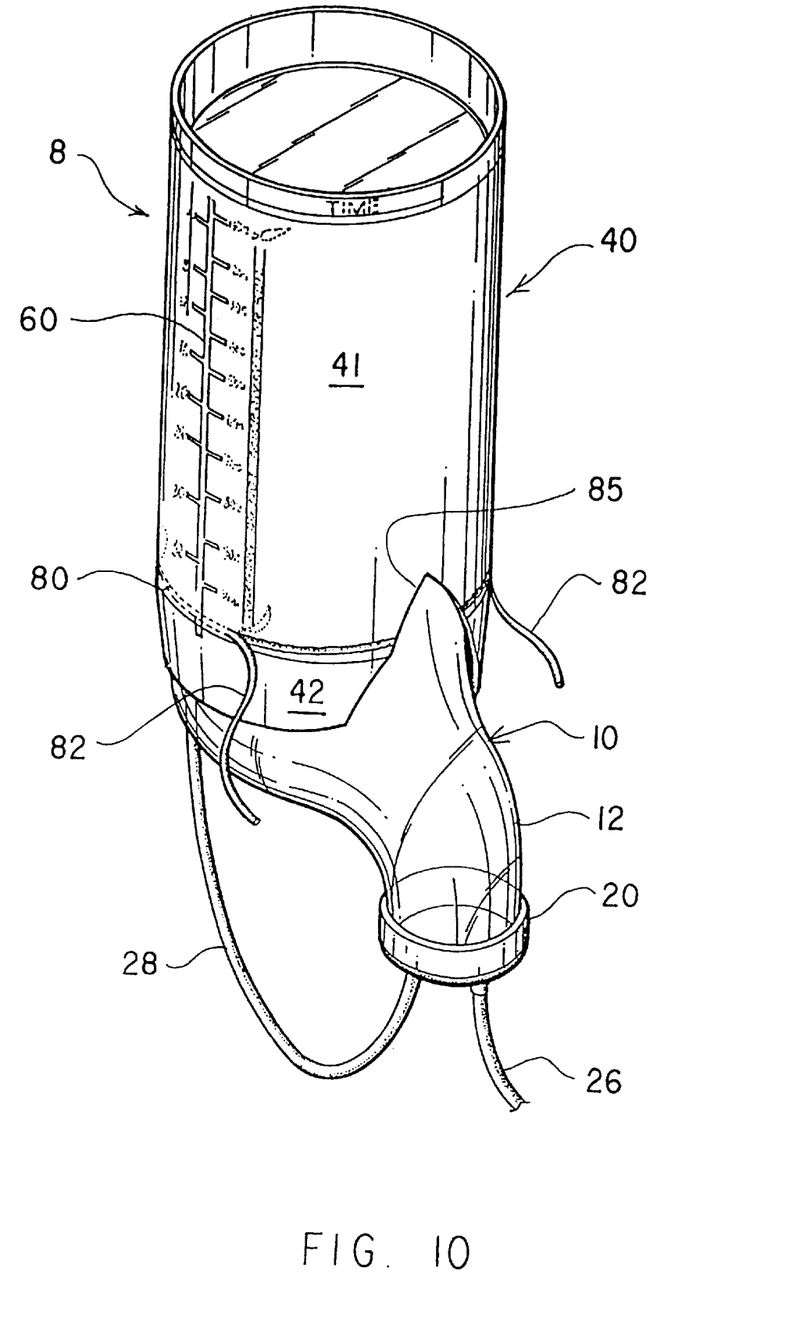
FIG. 10 is a perspective view depicting the decorative cover of FIG. 9 disposed over the embodiment of the feeding bottle of FIG. 8.

FIG. 9 is a rear perspective view of the embodiment of the decorative cover 40 for use with the embodiment of the feeding apparatus 8 wherein the feeding bottle 10 has an off-center neck 12. FIG. 10 is a perspective view depicting the decorative cover 40 of FIG. 9 covering the embodiment of the feeding bottle 10 having an off-center neck 12. This embodiment of the decorative cover 40 includes the features of the decorative cover 40 described in FIGS. 6 and 7. The decorative cover 40 of FIGS. 9 and 10 further includes a slit 85 extending from the neck-covering portion 41 to the main-body-covering portion 42. The slit 85 accommodates the curved design of the feeding bottle 10 which has an off-center neck 12. A peelable adhesive strip 80 having a length greater than the circumference of the decorative cover 40 is attached circumferencially around the neck-covering portion 42 of the decorative cover 40. The peelable adhesive strip 80 has two opposing ends 82 peelably disposed upon the decorative cover 40. The opposing ends 82 may be peeled from the decorative cover 40 for adhesive re-attachment to the neck-covering portion 42 after the neck-covering portion 42 has been gathered together to reduce the circumference thereof for securing the decorative cover 40 over the feeding bottle 10. FIG. 10 depicts the two opposing ends 82 peeled from the neck-covering portion 42 and ready for re-attachment around or under the neck 12 to secure the decorative cover 40 around the feeding bottle 10.

It is to be understood that the present invention is not limited to the sole embodiment described above, but encompasses any and all embodiments within the scope of the following claims.

I claim:

1. A feeding apparatus, comprising:
   a feeding bottle having a main body with a gripping area and a volumetric scale for measuring food portions, and a neck with an opening;
   a feeding cap sealingly attachable to the opening, the feeding cap having a first hole and a second hole;
   a feeding tube having a first end attached to the first hole of the feeding cap, and a second end having an adapter for connection of the feeding tube to a G.I. tube inserted into a stoma in the digestive track of a patient, whereby liquified food in the feeding bottle may pass through the feeding tube, through the G.I. tube and into the digestive track of the patient;
   an air inlet tube having a first end attached to the second hole of the feeding cap, and having a second end positionable above the level of food in the feeding bottle, the air inlet tube having an air passage for venting the feeding bottle to avoid creating a vacuum as food flows out and enable the continued flow of food out of the feeding bottle to the patient via the feeding tubes;
   a flow control valve disposed in communication with one of either the air passage of the air inlet tube or the feeding tube, said flow control valve being selectively positionable between an open position for allowing food-flow through the feeding tube, and a closed position for preventing food-flow;
   a transparent food-flow indicator disposed in communication with the feeding tube for enabling visual confirmation of the food-flow through the feeding tube;
   concealing means for concealing the contents of the feeding bottle;
   a strap sized and configured for supporting the feeding bottle; and
   a handle attached to the strap for hanging from a stand.

2. The feeding apparatus according to claim 1, wherein the feeding cap, feeding tube and air inlet tube are formed of a unitary construction.

3. The feeding apparatus according to claim 1, wherein the adapter is constructed to enable connection to G.I. tubes of varying internal diameter.

4. The feeding apparatus according to claim 1, further including a storage cap sealingly attachable to the opening, and for selective interchanging with the feeding cap during periods in which the feeding bottle is not being used.

5. The feeding apparatus according to claim 1, further including a tube holding means disposed upon the strap for holding the second end of the air inlet tube above the feeding bottle.

6. The feeding apparatus according to claim 1, wherein the transparent food-flow indicator is of a larger diameter than the feeding tube for easier viewing.

7. The feeding apparatus according to claim 1, wherein the concealing means comprises a decorative cover sized for fitted, removable disposition over the feeding bottle.

8. The feeding apparatus according to claim 7, further comprising a securing means for securing the fittedly disposed decorative cover over the feeding bottle.

9. The feeding apparatus according to claim 8, wherein the securing means comprises a peelable adhesive strip disposed upon the decorative cover.

10. The feeding apparatus according to claim 7, wherein the neck is narrower than the main body of the feeding bottle for easier securing of the decorative cover over the feeding bottle.

11. The feeding apparatus according to claim 1, wherein:
    the feeding bottle is non-transparent; and
    the concealing means is integral with the feeding bottle.

12. The feeding apparatus according to claim 1, wherein:
    the feeding bottle is non-transparent;
    the main body of the feeding bottle has a transparent portion, and further includes a volumetric scale on the transparent portion of the main body of the feeding bottle; and
    the concealing means is integral with the feeding bottle.

13. The feeding apparatus according to claim 1, further including decorative designs embossed upon the feeding bottle.

* * * * *